United States Patent
Hartmann et al.

(10) Patent No.: US 8,012,178 B2
(45) Date of Patent: Sep. 6, 2011

(54) DEVICE FOR ELASTICALLY STABILIZING VERTEBRAL BODIES

(75) Inventors: Stephan Hartmann, Solothurn (CH); Armin Studer, Langendorf (CH)

(73) Assignee: Synthes USA, LLC, West Chester, PA (US)

(*) Notice: Subject to any disclaimer, the term of this patent is extended or adjusted under 35 U.S.C. 154(b) by 1559 days.

(21) Appl. No.: 11/393,567

(22) Filed: Mar. 29, 2006

(65) Prior Publication Data

US 2006/0260483 A1 Nov. 23, 2006

Related U.S. Application Data

(63) Continuation of application No. PCT/CH03/00647, filed on Sep. 29, 2003.

(51) Int. Cl.
*A61B 17/70* (2006.01)
(52) U.S. Cl. .................................................. 606/255
(58) Field of Classification Search .......... 606/246, 606/250–266, 279; 623/17.11–17.16
See application file for complete search history.

(56) References Cited

U.S. PATENT DOCUMENTS

| | | | |
|---|---|---|---|
| 5,827,328 A * | 10/1998 | Buttermann | 623/17.13 |
| 6,206,882 B1 | 3/2001 | Cohen | |
| 6,267,764 B1 | 7/2001 | Elberg | |
| 6,440,169 B1 | 8/2002 | Elberg et al. | |
| 2003/0220643 A1* | 11/2003 | Ferree | 606/61 |

FOREIGN PATENT DOCUMENTS

| | | |
|---|---|---|
| CN | 88 2 01056 U | 8/1988 |
| EP | 0 667 127 | 8/1995 |
| GB | 2 382 304 | 5/2003 |
| JP | 56071539 | 6/1981 |
| JP | 2000337415 | 12/2000 |
| WO | WO 03/047442 | * 3/2002 |

OTHER PUBLICATIONS

Translated Office Action issued by Japanese Patent Office.

* cited by examiner

*Primary Examiner* — Thomas C. Barrett
*Assistant Examiner* — Samesh Boles
(74) *Attorney, Agent, or Firm* — Stroock & Stroock & Lavan, LLP

(57) ABSTRACT

A device for elastically stabilizing vertebral bodies includes at least two bone anchoring means, each having a central axis and a head segment. The device also includes elastic means that can be joined to the head segments of two adjacent bone anchoring means in such a manner that the longitudinal axis of the elastic means extends transversely to the central axes of the bone anchoring means. Under compressive loads, the elastic means has a progressive spring characteristic. The elastic means is manufactured from a metallic material and has a plurality of spring coils, of which at least two spring coils have a geometric dimension which is different from the other spring coils.

20 Claims, 4 Drawing Sheets

DEVICE FOR ELASTICALLY STABILIZING VERTEBRAL BODIES

CROSS REFERENCE TO RELATED APPLICATION

This is a continuation of International Patent Application No. PCT/CH2003/00647, filed Sep. 29, 2003, the entire contents of which are incorporated herein by reference thereto.

TECHNICAL FIELD OF THE INVENTION

The invention is directed to a device for the elastic stabilization of vertebral bodies. The device has only one spring element made from a metallic material and has a progressive spring characteristic under compressive loads.

BACKGROUND OF THE INVENTION

When treating damaged or tumorous bodies of the vertebra, usually rigid longitudinal supports are used which are anchored by bone anchoring means, (e.g., pedicle screws or pedicle hooks). In this manner, a movement of the stabilized bodies of the vertebra relative to one another can be prevented, so that the fusion of the adjacent bodies of the vertebra is promoted.

One known device to fix vertebral bodies is made up of a number of tulip-shaped pedicle screws, but instead of the conventional rigid longitudinal support, the screws are connected with individual helical spring elements. Although the length of the helical springs can be adjusted, only a modification of the pretensioning force of the helical spring elements is achievable.

Another known device to fix vertebral bodies is also made up of a number of tulip-shaped pedicle screws, but instead of the conventional rigid longitudinal support, the screws are connected with individual damping elements. A disadvantage of these damping elements is their manufacture from a biocompatible material, resulting in the damping element having linear spring characteristics.

A further device to fix vertebral bodies with a number of pedicle screws and elastic connecting parts provided between each two pedicle screws parallel to the longitudinal axis of the spinal column is also known. This device comprises elastic connecting parts with progressive spring characteristics. The elastic means comprises a helical spring, the central bore of which is filled with a visco-elastic material. A disadvantage of this known device is that by constructing the elastic means with two elements having different spring characteristics, an elaborate manufacturing process of the elastic means is required.

SUMMARY OF THE INVENTION

The object of the invention is therefore to produce a device for the stabilization of vertebral bodies that comprises only one spring element made from a metallic material and that has progressive spring characteristics under pressure.

The advantages achieved by the invention include the following:
 a sufficiently great elastic yielding and damping at small compressive forces. An adequate freedom of movement of the spinal column is therefore possible in this region;
 in the case of high pressure loads, no large spring travels are necessary to accept the compressive forces, so that an overload of the posterior elements can be avoided;
 with a spring element manufactured from a single biocompatible material, e.g. titanium, continuous progressive spring characteristics can be achieved.

In a preferred embodiment, the spring characteristic of the elastic means is continuous as shown in a force-travel diagram. At the same time, the elastic means can be constructed as a helical spring with a varying coil pitch.

Further constructions of a helical spring with progressive characteristics are feasible by, for example:
 manufacturing a helical spring which, measured parallel to the longitudinal axis, has slots with different widths x at least between two adjacent spring coils, or
 manufacturing a helical spring from a spring material, the cross-sectional areas of which, when viewed perpendicular to the longitudinal axis and measured parallel to the longitudinal axis, have different heights h at least between two adjacent coils.

In another embodiment, the elastic means are constructed as a flat, meander-shaped spring with a plurality of spring coils provided successively parallel to the longitudinal axis, wherein each coil has an inflecting loop with an axis of bending.

Depending on the embodiment, the distances L between the axes of bending and the longitudinal axis may be constant on both sides of the longitudinal axis, or the spring coils may be so implemented, that the distance L1 between the at least one axis of bending, provided on the left side of the longitudinal axis, and the longitudinal axis and the distance L2 between the at least one axis of bending, provided on the right side of the longitudinal axis, and the longitudinal axis, are different.

In yet another embodiment, each spring coil comprises restraining means which limit the allowable spring travel of the respective spring coil. The restraining means preferably comprises at least one lug per coil that limits the spring travel s of the respective coil.

Depending on the construction of the lugs, the spring travel s limited by at least one lug can be different for at least two spring coils.

The meander-shaped spring can have n number of spring coils, while each coil has a different spring characteristics i, i.e., for example $i_1 < i_j < i_n$.

In a further embodiment, the wall thickness of the spring material of at least two inflecting loops are different, so that the spring characteristics are different for these two coils.

In yet another embodiment, the elastic means comprise connecting means on their axially outer ends, which are suitable for the fixing of the elastic means on the bone anchoring means. For example, one of the two connecting parts can be constructed as a rod which is coaxial with the longitudinal axis, whereas the second connecting part can be constructed as a sleeve with a central bore that is coaxial with the longitudinal axis and accommodates a rod-shaped longitudinal support. On the other hand at least one connecting part is feasible, that can be connected by means of a hinged joint with, for example, a rod-shaped longitudinal support.

BRIEF DESCRIPTION OF THE DRAWINGS

The detailed description will be better understood in conjunction with the accompanying drawings, in which like reference characters represent like elements as follows.

DETAILED DESCRIPTION OF THE INVENTION

Figure 1:
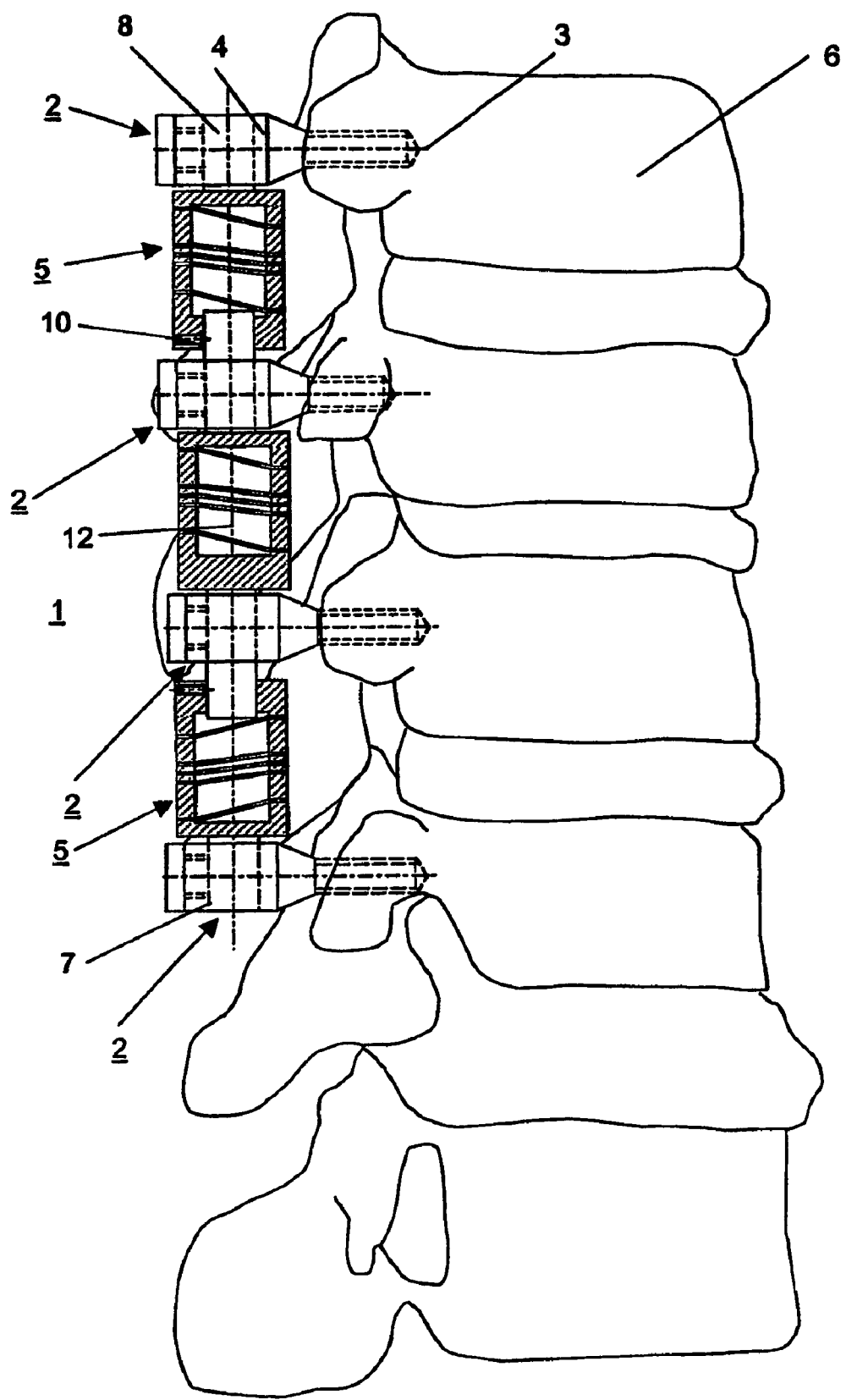
FIG. 1 shows an embodiment of a device for the stabilization of several bodies of the vertebra.

FIG. 1 illustrates an embodiment of a device 1 for the stabilization of adjacent bodies 6 of the vertebra. Several bone anchoring means 2, formed, for example, as pedicle screws, are screwed into the pedicles of the bodies 6 of the vertebra to be joined such that their central axes 3 are arranged transversely to the longitudinal axis of the spinal column. The head segments 4 of the bone anchoring means 2 are coaxial with the central axes 3 of the bone anchoring means 2 and have channels 7 which extend transversely to the central axis 3. The rod-shaped connecting parts 8 of the elastic means 5 can be introduced into these channels 7, so that the elastic means 5, constructed in this case as helical springs, can be displaced relative to the channels 7 and parallel to the longitudinal axis of the spinal column before they are fixed relative to the bone anchoring means 2 by means of screws 10 provided in the head segments 4. The elastic means 5 can be elastically deformed axially relative to their longitudinal axes 12 and bent so that the spring travels s (see FIG. 4) of the bone anchoring means are also parallel to the longitudinal axis 25. According to the embodiment illustrated in FIG. 2, the two axially outer elastic means 5 are fitted with connecting parts 16a, 16b, while the middle elastic means 5 comprise two rod-shaped, coaxial connecting parts 16a (see FIG. 2).

Figure 2:
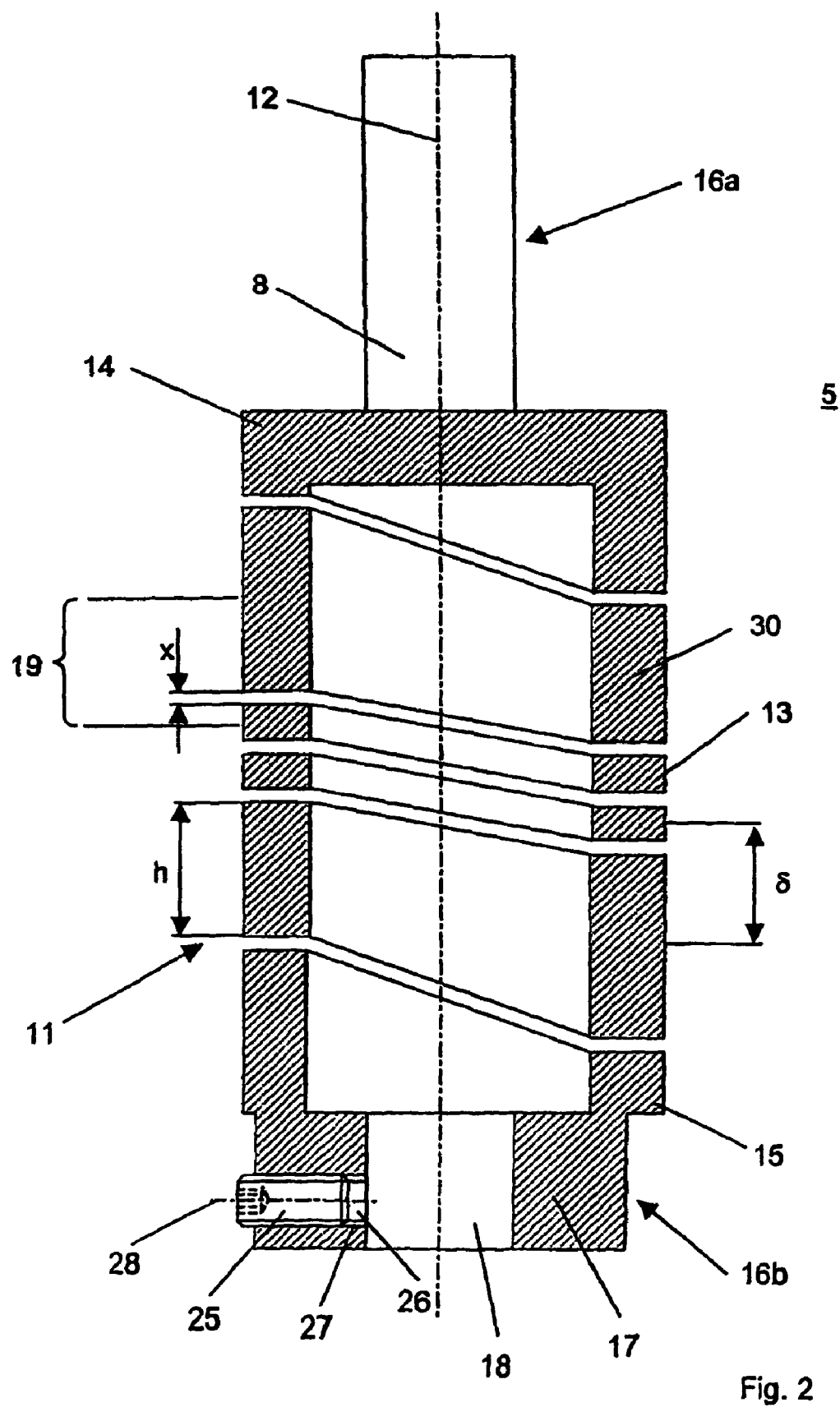
FIG. 2 is a longitudinal section view through the elastic means of an embodiment of the device.

FIG. 2 illustrates an embodiment of the elastic means 5 in the form of a helical spring 11, the material of which has a rectangular cross-section 13 that is perpendicular to the longitudinal axis 12, while the height h of the cross-sectional area 13, measured parallel to the longitudinal axis 12, varies. By virtue of the increasing towards the ends 14, 15 of the helical spring 11 height h of the cross-sectional area 13, the pitch δ of the spring coils also increases towards the ends 14, 15 of the helical spring 11. In the embodiment illustrated, the width x of the slot remains constant along the entire length of the helical spring 11. The helical spring 11 is circular with a cross-section perpendicular to the longitudinal axis 12 and has at each of its ends 14, 15, which intersects the longitudinal axis 12, a connecting means 16, that fixes the helical spring 11 on a bone anchoring means 2 (shown in FIG. 1.). The first connecting means 16a, provided on the first end 14 of the helical spring 11, is constructed as a rod 8 that is coaxial with the longitudinal axis 12. The second connecting means 16b, provided on the second end 15 of the helical spring 11, is constructed as a sleeve 17 and has a central bore 18 that is coaxial with the longitudinal axis 12. Both connecting means 16a, b are firmly joined with the helical spring 11. By virtue of the varying pitch δ of the spring coils 19 of the helical spring 11, a progressive spring characteristic is achieved. For the fixing of a rod-shaped part in the central bore 18, a fixing screw 25 is provided that can be screwed into a bore 26 having a complementary inside thread 27 with a bore axis 28 that extends transversely to the longitudinal axis 12 and is pressed with its front end against a rod (not illustrated) introduced into the central bore 18.

Figure 3:
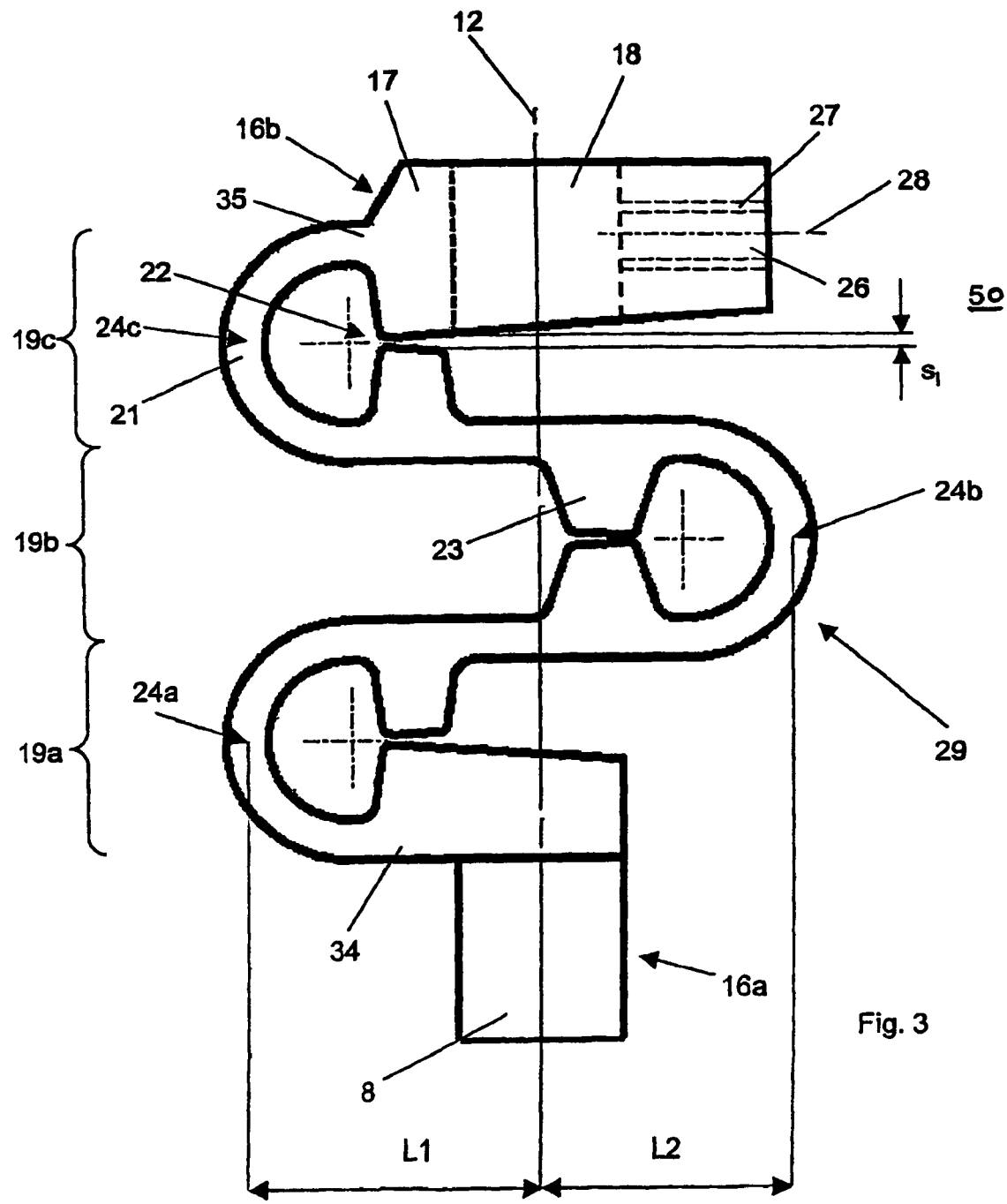
FIG. 3 is a view of the elastic means of another embodiment of the device for the stabilization of several bodies of the vertebra.

FIG. 3 shows another embodiment of the elastic means 5. Elastic means 50 comprises a spring 29 with a plurality of spring coils 19 situated in one plane. Each of the three coils 19a, 19b, 19c has an inflecting loop 21 subjected to bending and restraining means 22. The restraining means 22 in this case are two lugs 23, which after reaching the spring travel permissible per coil 19, each abut against one another and prevent a further springing of the relevant coil 19. Each of the inflecting loops 21 of the three spring coils 19a, 19b, 19c has an axis 24a, 24b, 24c of bending, while the length L1 of the lever arm affecting the bending to the left of the longitudinal axis 12 is greater than the length L2 of the lever arm affecting the bending to the right of the longitudinal axis 12. Instead of lever arms of different lengths, the spring travels $s_i$ per spring coil 19, allowed by the restraining means 22, may also be different. Similar to the embodiment illustrated in FIG. 2, at both of its ends 34, 35, intersecting the longitudinal axis 12, the spring 29 has a connecting means 16 suitable for the fixing of the elastic means 50 on the end of the bone anchoring means 2 (FIG. 1). The first connecting means 16a, provided on the first end 34 of the spring 29 is constructed as a rod 8 that is coaxial with the longitudinal axis 12, whereas the second connecting means 16b, provided on the second end 35 of the spring 29, is constructed as a sleeve 17 and comprises a central bore 18 that is coaxial with the longitudinal axis 12. Both connecting means 16a,b are firmly joined with the spring 29. For the fixing of a rod-shaped part in the central bore 18, a fixing screw (not illustrated) is provided that can be screwed into a bore 26, having a complementary inside thread 27 and a bore axis 28 extending transversely to the longitudinal axis 12, and have its front end pressed against a rod (not illustrated) introduced into the central bore 18.

Figure 4A:
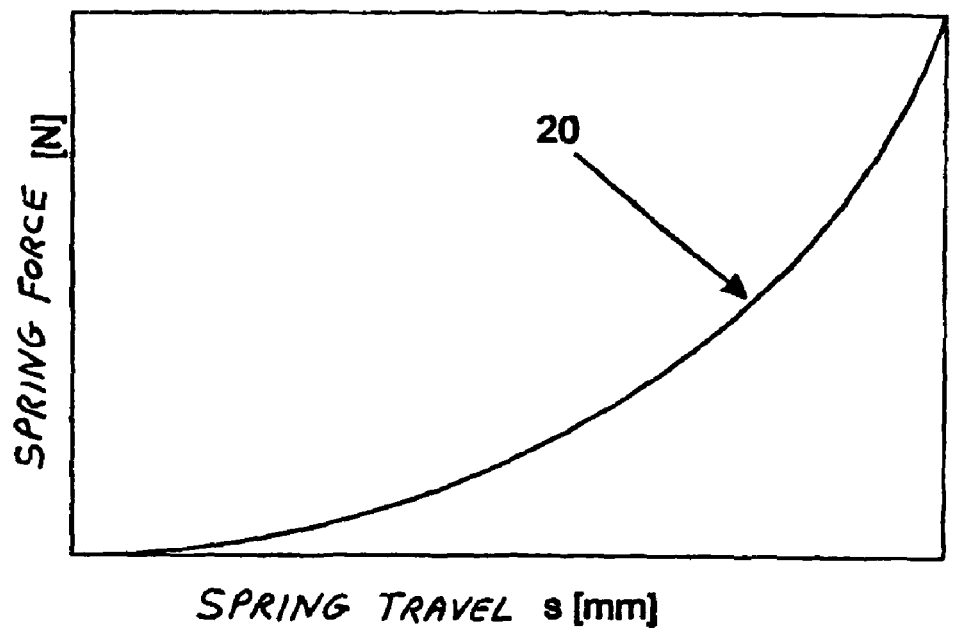
FIGS. 4a and 4b show the spring characteristics in travel-force diagrams (spring travel on abscissa and spring force on ordinate) of the elastic means of the embodiment shown in FIG. 2.
Figure 4B:
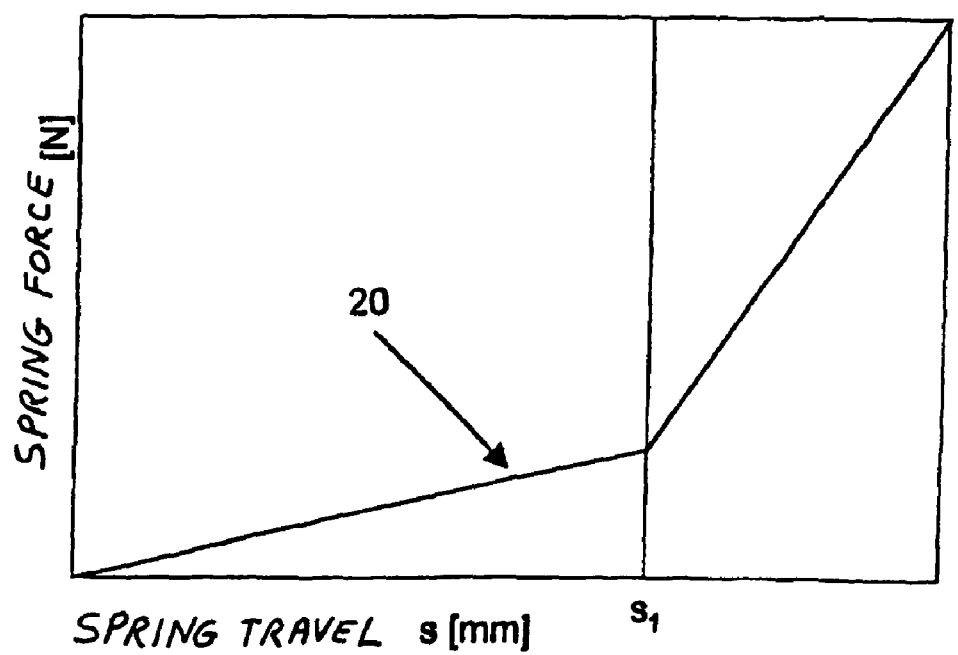

FIGS. 4a and 4b illustrate the spring characteristics 20 in force-travel diagrams for the embodiment of the elastic means illustrated in FIG. 2. The spring characteristic 20 is progressive over the entire spring travel. Such a spring characteristic 20 can be achieved, for example, by constructing the elastic means 5 as a helical spring 11 with pitch δ that continuously varies along the longitudinal axis 12.

The spring characteristic illustrated in FIG. 4b can be realized by implementing the elastic means 5 as a meander-shaped spring 29. According to FIG. 4b, the spring characteristic 20 is uneven and at a spring travel $s=s_i$ it has an inflection point, that can be realised, for example, by the closing of the restraining means 22 of a spring coil 19.

The invention claimed is:

1. A device for dynamic stabilization of vertebral bodies, the device comprising: at least a first and second bone anchoring device each having a head segment; and an elastic means having a first end section, a second end section and a longitudinal axis, the first end section of the elastic means connectable to the head segments of the first bone anchoring device and the second end section of the elastic means connectable to the head segment of the second bone anchoring device such that the longitudinal axis extends between the first and second bone anchoring devices, wherein: the elastic means is made of a metallic material and comprises a plurality of helical spring coils having a pitch δ, at least two of the spring coils have at least one geometric dimension which is different than the other of the spring coils, and the pitch of the spring coils varies continuously along the longitudinal axis, and under a compressive load, the elastic means has a progressive spring characteristic, wherein the pitch of the helical spring coils increases from center towards the ends of the plurality of helical spring coils.

2. The device of claim 1 wherein the spring characteristic of the elastic means has a continuously progressive force-travel curve as plotted on a diagram of spring travel versus spring force.

3. The device of claim 1 wherein, when measured parallel to the longitudinal axis, the helical spring coils have a slot having a width x between adjacent spring coils, and the width x between two adjacent spring coils varies.

4. The device of claim 1 wherein the helical spring is manufactured from a spring material, and the cross-sectional area of the spring coils perpendicular to the longitudinal axis have a height h measured parallel to the longitudinal axis, wherein the height h of the cross-sectional area of two adjacent spring coils varies.

5. The device of claim 1 wherein the elastic means comprises at the first and second end section connecting parts suitable for the fixing of the elastic means to the bone anchoring means.

6. The device of claim 5 wherein at least one connecting part is a rod that is coaxial with the longitudinal axis.

7. The device of claim 5 wherein at least one connecting part is a sleeve having a central bore that is coaxial with the longitudinal axis.

8. The device of claim 5 wherein at least one connecting part comprises a hinged joint.

9. The device of claim 1 wherein the cross sectional area of the coil springs perpendicular to the longitudinal axis have a height h measured parallel to the longitudinal axis, wherein the height h increases from the center towards the ends of the plurality of the helical spring coils.

10. The device of claim 9 wherein, when measured parallel to the longitudinal axis, the helical spring coils have a slot width x between adjacent spring coils, and the slot width x remains constant along the entire plurality of helical spring coils.

11. The device of claim 1 wherein the helical spring coils are circular in shape.

12. The device of claim 11 wherein the diameter of the plurality of spring coils is constant.

13. The device of claim 1 the cross sectional area of the spring coils perpendicular to the longitudinal axis is rectangularly shaped.

14. A device for the elastic stabilization of bodies of the vertebra, the device comprising:
at least a first and second bone anchoring device each having a head segment; and
an elastic means having a first end section, a second end section, a longitudinal axis and a center located between the first end section and the second end section, the first end section of the elastic device connectable to the head segments of the first bone anchoring device, the second end section of the elastic device connectable to the head segment of the second bone anchoring device such that the longitudinal axis extends transversely between the first and second bone anchoring devices, wherein:
the elastic means is made of a metallic material, and comprises a plurality of spring coils having a pitch δ that continuously increases along the longitudinal axis from the center towards the ends of the plurality of spring coils, of which at least two of the spring coils have at least one geometric dimension which is different than the other of the spring coils, and under a compressive load, the elastic means has a progressive spring characteristic.

15. The device of claim 14 wherein when measured parallel to the longitudinal axis, the helical spring coils have a slot width x between adjacent spring coils, and the slot width x remains constant along the entire plurality of helical spring coils.

16. The device of claim 14 wherein the cross sectional area of the coil springs perpendicular to the longitudinal axis have a height h measured parallel to the longitudinal axis, wherein the height h increases from the center towards the ends of the plurality of the helical spring coils.

17. The device of claim 16 wherein the helical spring coils are circular in shape.

18. The device of claim 16 wherein the diameter of the plurality of spring coils is constant.

19. The device of claim 14 the cross sectional area of the spring coils perpendicular to the longitudinal axis is rectangularly shaped.

20. A device for the elastic stabilization of bodies of the vertebra, the device comprising:
at least a first and second bone anchoring device each having a head segment; and
an elastic means having a first end section, a second end section, a longitudinal axis and a center located between the first end section and the second end section, the first end section of the elastic device connectable to the head segments of the first bone anchoring device, the second end section of the elastic device connectable to the head segment of the second bone anchoring device such that the longitudinal axis extends transversely between the first and second bone anchoring devices, wherein the elastic means is made of a metallic material, and comprises a plurality of spring coils having a pitch δ, a cross sectional area perpendicular to the longitudinal axis and a slot width x between adjacent spring coils,
wherein the pitch δ continuously increases along the longitudinal axis from the center towards the ends of the plurality of spring coils, the cross sectional area of the spring coils have a height h measured parallel to the longitudinal axis that increases from the center towards the ends of the plurality of the helical spring coils, and the slot width x remains constant along the entire plurality of helical spring coils, and under a compressive load, the elastic means has a progressive spring characteristic.

* * * * *